United States Patent [19]

Christensen

[11] Plant 4,664

[45] Mar. 10, 1981

[54] ROSE PLANT

[75] Inventor: Jack E. Christensen, Ontario, Calif.

[73] Assignee: Armstrong Nurseries, Inc., Ontario, Calif.

[21] Appl. No.: 87,809

[22] Filed: Oct. 24, 1979

[51] Int. Cl.[3] ..... A01H 5/00
[52] U.S. Cl. ..... Plt./8
[58] Field of Search ..... Plt./8

*Primary Examiner*—Robert E. Bagwill

*Attorney, Agent, or Firm*—William H. Elliott, Jr.; Andrew R. Klein

[57] ABSTRACT

A hybrid miniature rose of the dwarf bush type, many-branched and upright in habit. Blooms are of average size or larger for miniature roses, usually occurring three or four to a stem, but occasionally singly. The bloom has from 16 to 22 petals, generally, and the same coloration occurs on inside, intermediate, and outside petals and on the inner and outer surfaces thereof, this color being a bright golden yellow which fades after several days to a less bright shade of the same color.

1 Drawing Figure

This invention relates to a new class of hybrid miniature rose. The plant is an outdoor seedling of the dwarf bush type, cultivated for cut flowers and for garden decoration. Its hardiness is untested. It was propagated by Jack E. Christensen in Ontario, Calif., having as its seed parent "Gingersnap" (U.S. Plant Pat. No. 4,330) and, as its pollen parent, "Magic Carrousel" (U.S. Plant Pat. No. 3,601). It holds its distinguishing characteristics through succeeding propagations by cuttings and by budding.

The new variety bears its flowers sometimes singly, but usually three or four to a stem, in irregular clusters on stems which are strong, medium to long, for a miniature rose. The plant blooms very abundantly outdoors, and nearly continuously during the growing season. It has a slight tea fragrance.

This new miniature rose cultivar may be distinguished from its seed parent, Gingersnap, by the following combination of characteristics:

Gingersnap bears flowers of relatively uniform bright orange coloration, whereas the new rose bears deep yellow flowers.

Gingersnap has significantly more petals, from 25 to 36, than does the new cultivar, which as from 16 to 22 petals.

The new rose is classed as a hybrid miniature, whereas Gingersnap falls in the hybrid floribunda class.

This new miniature rose cultivar may be distinguished from its pollen parent, Magic Carrousel, by the following combination of characteristics:

Magic Carrousel bears flowers of red and white coloration, whereas the new cultivar bears deep yellow flowers.

The new rose has significantly fewer petals, from 16 to 22, than does Magic Carrousel, which has from 24 to 30 petals.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is short to average in length and of average caliper, being erect and stiff and moderately rough with numerous stipitate glands. The color is between Moderate Yellow Green, 5GY5/6, and Moderate Yellow Green, 2.5GY5/5.

Before the calyx breaks, the bud is medium size for miniature roses. It is medium-length, pointed and ovoid in form, with stipitate glands on the surface of the bud, and usually with slender foliaceous parts extending beyond the tip of the bud equal to one-half or more of its length.

As the calyx breaks, the color is near Brilliant Yellow, 2.5Y9/9.

The inner surface of the sepals is lined with a fine tomentum; margins are lined with stipitate glands and hairs.

As the first petal opens, the bud is average in size, for miniature roses, medium-length, pointed and ovoid in form. The color on the outside of the petal is between Vivid Yellow, 2.5Y8/12, and Vivid Yellow, 5Y8/12. The inside of the petal is the same coloration as the outside. The bud opens up well and is not prevented from opening by cold, hot, wet or dry weather.

BLOOM

The size of the bloom when fully open is from average to large for miniature roses, being from 1 inch to 1.5 inches. The petalage is double, with from 16 to 22 petals, plus from 0 to 5 petaloids arranged regularly. The bloom is high centered at first, the petals remaining somewhat tightly cupped, with tips reflexed slightly outward, becoming later at maturity more loosely cupped, with tips reflexed outward.

The petals are of medium thickness, with both inside and outside being slightly satiny. The outside petals are broadly obovate in shape, while the intermediate and inside petals are narrowly obovate. The colors may be modified by being shaded and/or washed with other colors.

The paragraph immediately following describes color values observed in a flower newly opened in the month of June. The plant had been grown outdoors in Ontario, Calif.

The same coloration was noted in all petals, namely outside, intermediate and inner petals. The outer surface was between Brilliant Yellow, 2.5Y9/9, and Brilliant Yellow, 5Y9/9, in color. The inner surface was the same as the outer surface, but the base of the petal suffused to more near Brilliant Yellow, 5Y9/9.

The paragraph immediately following describes the color values observed in a bloom which had been open for three days, outdoors, in the month of June. The plant had been grown outdoors, in Ontario, Calif.

The outer and inner surfaces of both the outside petals and inside petals were the same, the color being lighter than Brilliant Yellow, 5Y9/9.

The general color effect of the newly opened flower is between Brilliant Yellow, 2.5Y9/9, and Brilliant Yellow, 5Y9/9. The bloom after being three days open gives a general color effect of being lighter than Brilliant Yellow, 5Y9/9. The petals persist, fading to much lighter than Brilliant Yellow, 5Y9/9, and are not particularly affected by cold, hot, wet, or dry weather.

The flower on the bush in the garden persists for from 4 to 5 days in the month of June, in the locality named. Cut roses grown outdoors and kept at living-room temperatures last from 3 to 5 days in the month of June.

REPRODUCTIVE ORGANS

There are many stamens, arranged regularly about the pistils, a few being tucked in the calyx.

Filaments are medium-length, and near Vivid Yellow, 5Y8/12, in color. Most are with anthers.

The anthers are medium size to large, all opening approximately at once. The color of the margins of the newly opened anther is near Vivid Yellow, 5Y8/12. The central portion is near Vivid Greenish Yellow, 7.5Y8/12, in color.

Pollen is moderate, and near Vivid Yellow, 5Y8/12, in color.

The pistils are of average number, for miniature roses, being approximately 50 in number.

The styles are moderately even, of average length and caliper, and somewhat bunched. The color is near Brilliant Greenish Yellow, 7.5Y9/8.

The stigma is between Dark Reddish Orange, 7.5R4/11, and Dark Reddish Orange, 10R4/9, in color.

Most of the ovaries are enclosed in the calyx.

Half-mature hips were of average length, ovoid and near Strong Yellow Green, 2.5GY7/10, in color, smooth and with fleshy walls.

The hip sepals are permanent, medium-length and straight. On the inside, they are near Light Yellow Green, 7.5GY9/4, while on the outside they are near Strong Yellow Green, 7.5GY7/9, in color.

There are a few seeds, from 2 to 6 in number, and these are usually small to medium-size.

FOLIAGE

The compound leaves usually comprise 3 to 5 leaflets. They are moderately abundant, medium in size, for miniature roses, moderately heavy and semi-glossy. The leaflets are obovate, with apex slightly mucronate, base acute, and margin irregularly serrate.

The mature foliage displays upon its upper surface a color which is between Moderate Olive Green, 7.5GY4/4, and Moderate Olive Green, 5GY4/3. The under surface is near Moderate Yellow Green, 2.5GY5/5, overlaid with gray bloom.

The young foliage on its upper surface is near Moderate Yellow Green, 2.5GY5/5, washed and edged with near Dark Red, 5R3/7. Its under surface is between gray and Dark Red, 5R3/7.

The rachis is average in size, grooved on its upper side, with some stipitate glands on the edges. The under side is smooth, with stipitate glands.

The stipules are medium-length to long, medium-width, with long points turning out at an angle of less than 45°.

The plant displays a more than average resistance to mildew, when compared with other varieties now in commerce under comparable conditions, when grown at Ontario, Calif.

GROWTH

The plant is a bushy dwarf, upright in habit and much branched. It displays a very vigorous growth. The canes are moderately heavy, for miniature roses.

The main stems are near Moderate Reddish Brown, 7.5R3/6, in color, on the sunny side; on the shaded side, the color is near Brilliant Yellow Green, 7.5GY8/7. They bear few large prickles, which are medium-length to long, almost straight to hooked slightly downward, with long, narrow base. Their color is near Strong Brown, 2.5YR4.7, at the base and near Brilliant Greenish Yellow, 7.5Y9/8, at the point. There are no small prickles and no hairs.

The branches have the same coloration as the main stems. There are several large prickles which are the same in size and form as those on the main stems, but in coloring they are near Strong Red, 5R4/12, at the base, with the point being near Brilliant Greenish Yellow, 7.5Y9/8. There are no small prickles and no hairs.

New shoots are near Moderate Yellow Green, 2.5GY5/5, in color, and are washed with near Dark Red, 5R3/7. There are several large prickles which are the same in size and form as those on the main stems and branches. Their coloration is near Dark Red, 5R3/7. There are no small prickles and no hairs.

I claim:

1. A new and distinct variety of rose plant of the hybrid miniature class, substantially as herein shown and described, and being further characterized in the well-formed golden yellow buds and blooms, the double petalage of which displays substantially the same coloration in outer, intermediate and inner petals and on the inner and outer surfaces of each petal, the bush being of upright and vigorous growth habit and profusely producing flowers of heavy substance and good color retention.

* * * * *

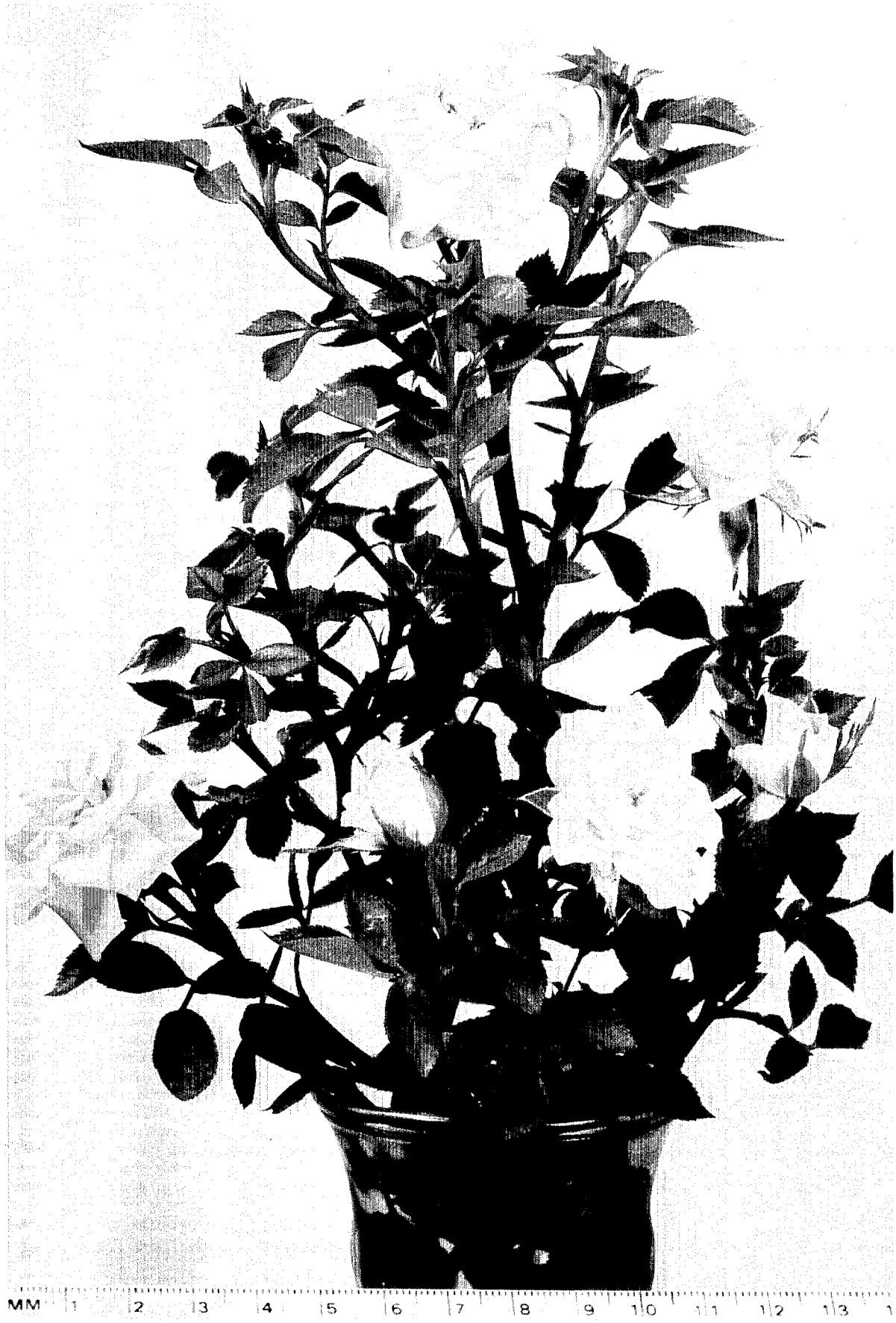
MM 1 2 3 4 5 6 7 8 9 10 11 12 13 1